United States Patent [19]

Austin et al.

[11] Patent Number: 4,515,589

[45] Date of Patent: May 7, 1985

[54] PERISTALTIC PUMPING METHOD AND APPARATUS

[76] Inventors: Jon W. Austin, 1909 E. Camino de Los Ranchos, Phoenix, Ariz. 85022; Cecil C. Vaughn, 421 N. 18th St., Phoenix, Ariz. 85006

[21] Appl. No.: 510,656

[22] Filed: Jul. 5, 1983

Related U.S. Application Data

[63] Continuation-in-part of Ser. No. 246,408, Mar. 23, 1981, abandoned.

[51] Int. Cl.³ .................... A61M 5/00; F04B 43/12
[52] U.S. Cl. .................... 604/122; 417/477; 222/214; 604/153
[58] Field of Search .......... 417/477, 475, 53; 222/214; 128/DIG. 12; 604/122, 123, 153

[56] References Cited

U.S. PATENT DOCUMENTS

| | | | |
|---|---|---|---|
| 3,105,447 | 10/1963 | Ruppert | 417/475 |
| 3,717,174 | 2/1973 | Dewall | 604/34 X |
| 3,784,323 | 1/1974 | Sausse | 417/477 X |

*Primary Examiner*—Richard E. Gluck
*Attorney, Agent, or Firm*—Gregory J. Nelson

[57] ABSTRACT

A peristaltic pump in which fluid is displaced towards the outlet of the pump by a rotating member which engages a section of tubing. The tubing comprises an outer tubing and an inner tubing with an annular airspace maintained therebetween and vented to atmosphere. When a positive hydrostatic head is maintained above the pump head level, the inner tubing will expand and fill. When the fluid level drops below the pump head level, the inner tube collapses, closing off the tube so there is no fluid volume to displace and the pump output stops to prevent entrainment of air into the patient's circulation. An occluding valve having a normlly closed position may also be provided at the inlet to the pumping section.

3 Claims, 11 Drawing Figures

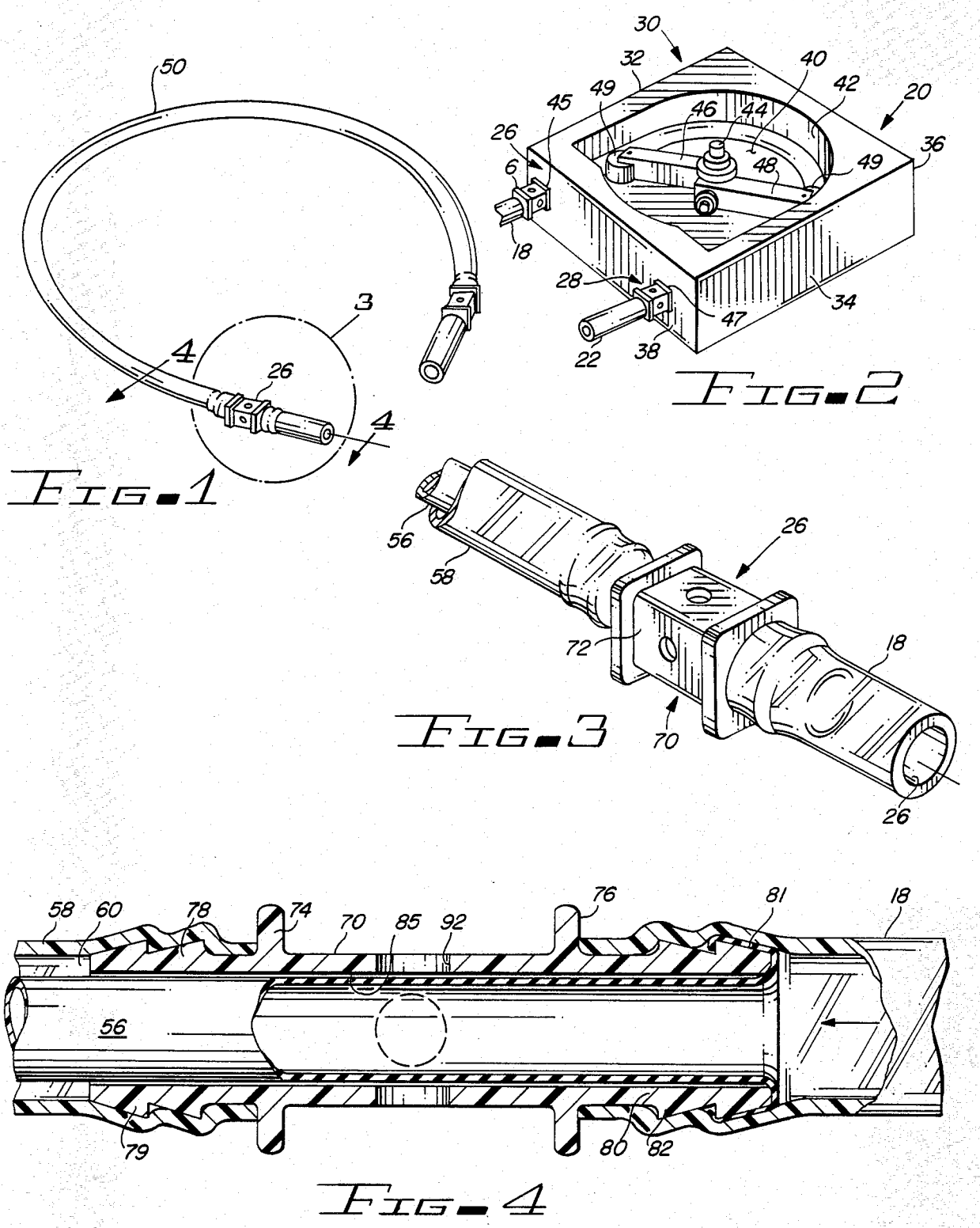

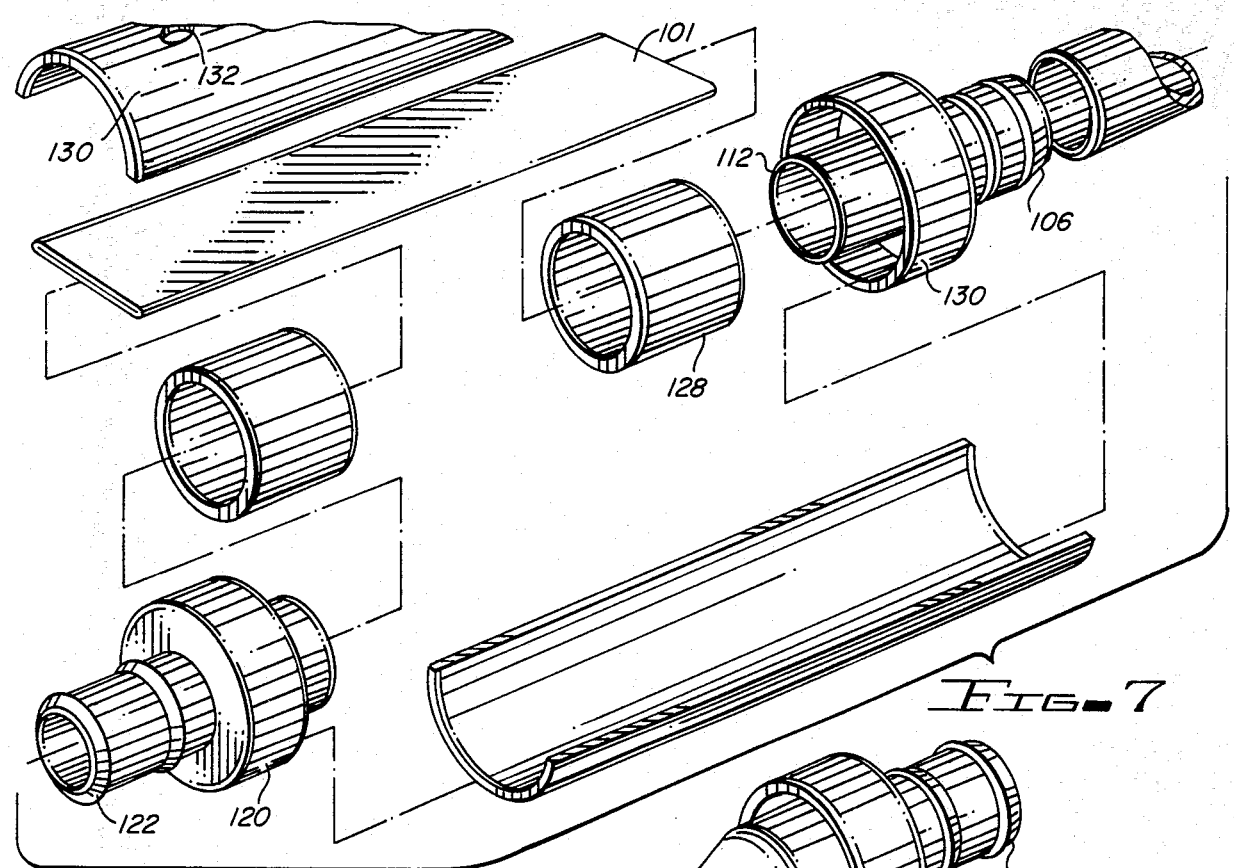
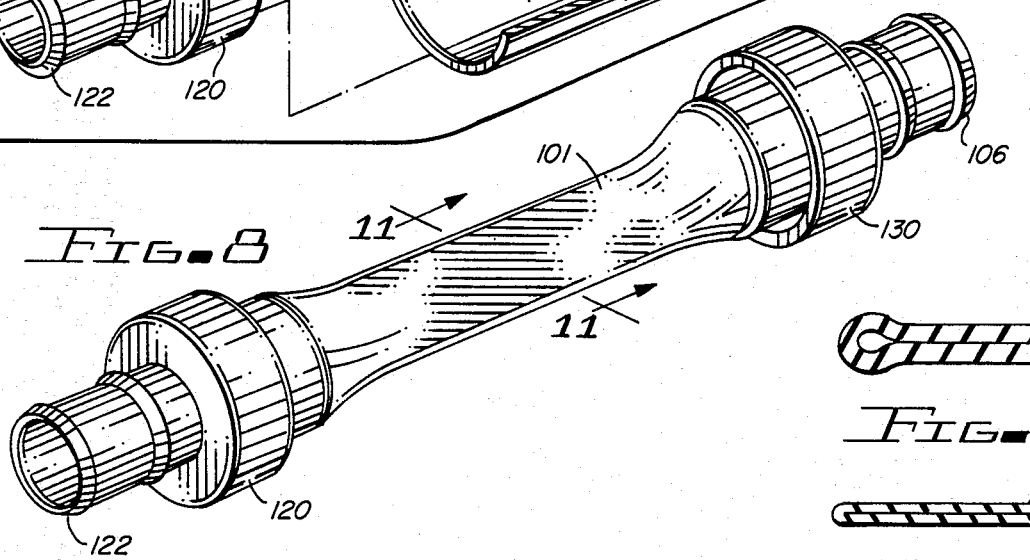
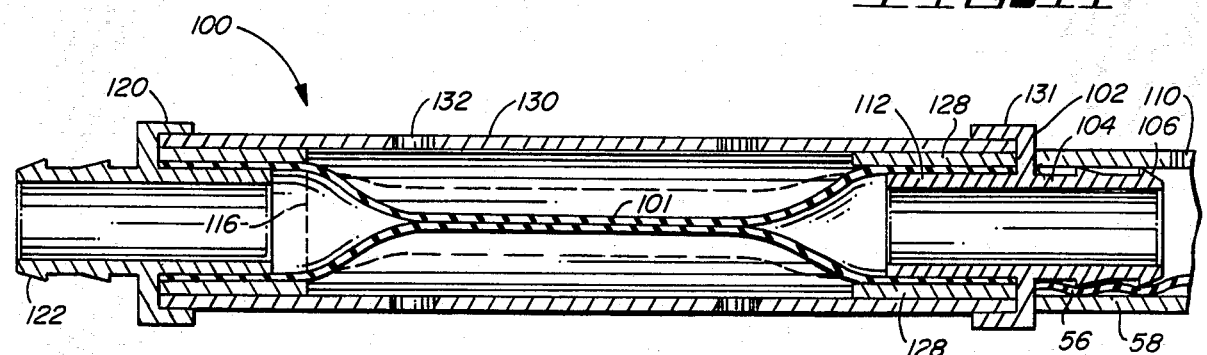

PERISTALTIC PUMPING METHOD AND APPARATUS

The present application is a continuation-in-part of application Ser. No. 246,408, now abandoned entitled "peristaltic pumping method and apparatus", filed Mar. 23, 1981.

The present invention relates to pumps and more particularly relates to peristaltic pumps of the type in which a liquid is forced through an elastic tube by progressively compressing the tube at spaced-apart locations along the tube. Pumps of this general type have particular application in the medical field for transferring blood and fluids between a patient and an extracorporeal device.

Most pumps used for extracorporeal circulation devices are peristaltic. Pumps of this type are commonly used in open-heart surgery for circulating blood between the patient and a heart-lung machine. Pumps of similar design are used in dialysis procedures for transferring blood between a patient and a dialyser and peristaltic pumps are also used for positive pumping of IV solutions.

Peristaltic pumps are volumetric pumps which progressively compress a flexible tube to propel liquid along the tube under the influence of rotating member which contacts the tube at spaced-apart points. A principal advantage of pumps of this type is that they are inherently simple having no internal valves. Blood or other fluid passes through a chemically inert tube that can be easily sterilized. The blood or pumped fluid does not come into direct contact with the rotating member of the pump.

Certain disadvantages arise from the inherent characteristics of these type pumps when utilized in perfusion and similar medical applications. A physiologically adequate perfusion cannot be achieved when venous return to the extracorporeal apparatus is unstable. Approximately 80% of the total blood volume of an adult is contained in the venous and capillary network. It is not surprising then that small changes in venous pressure can reflect large changes in blood volume. Cardiopulmonary bypass can significantly alter venous blood flow characteristics.

When venous return to the extracorporeal apparatus is by gravity into an open reservoir, a decrease in venous return to the oxygenator without a corresponding output reduction can lead to accidental emptying of the oxygenator and infusion of air. Independent factors control the rate of blood input and the rate of blood output from the bubble oxygenator. The rate of blood inflow is basically controlled by the position and size of the venous cannula and by the height difference between the venous cannulation site and the oxygenator. The output of blood is directly controlled by the rate of blood pumping.

Venous return to the extracorporeal apparatus by a venous blood pump has advantages of both simplicity and flow metering ability. However, direct cannulation of the venous system when using a roller type blood pump poses some significant dangers. A conventional roller pump has the capability of generating high inlet negative pressures. Aspiration of air through the cannulation site has been reported. Damage to the atrium or vena cava wall is also a danger when high negative pressures develop. When occlusion of the inlet tube occurs it is possible to aspirate air through a tubing connector. Cavitation, or drawing of dissolved gasses from the blood, occurs when strong negative pressures develop.

Leaks on the negative side of a roller blood pump are dangerous. Air may be rapidly aspirated if a leak occurs on the negative side of a roller blood pump. Whe using a venous blood pump an additional pump is required beyond what is required for gravity drainage systems. The elimination of an additional pump from the circuit will eliminate the hazard associated with having an additional extracorporeal blood pump.

No matter what method is used to accomplish venous return, when venous volume depletion starts, fluctuations in blood flow rates also occur. When the great veins are emptied of their contents and venous collapse occurs, further increases in suction do not accomplish more blood flow but only further increases venous collapse.

Pumps can be found in the prior art which are provided with regulating devices to control the available pumping volume so the output is controlled as a function of inlet pressure. For example, U.S. Pat. No. 3,784,323 shows a peristaltic pump in which the material and thickness of the wall of the tube are selected so there is a predetermined differential pressure between the exterior and interior of the tube. Collapse of the tube will occur to restrict the flow rate of the liquid as a function of the pump inlet pressure. Therefore, the flow rate will become restricted and lessened in the event the supply of the vein decreases to prevent collapse and possible damage to the wall of the vessel.

Briefly, the present invention provides an improved peristaltic pumping method and apparatus. The apparatus of the present invention includes a peristaltic pump having a housing defining a stator or raceway. The peristaltic pumping action is produced by a head or rotor having rollers engaging a flexible pumping section of tubing comprising the pumping section. One end of the pumping section is connected to a fluid reservoir such as a blood reservoir in an oxygenation system. The pumping section comprises an inner tube and an outer tube with the annular area between the two tubes vented to atmosphere. When a positive hydrostatic pressure head is maintained above the pump head level, the inner tubing will be filled from the reservoir. When the fluid level drops below a pre-determined pump head level, the inner tube will progressively collapse until there is no volume to displace and the pump output stops and entrainment of air into the patient's system is avoided. In a further improvement, the pumping section is provided with an inlet occlusion valve fabricated of a thin walled elastic material having a normally flattened shape with a cross-sectional area that increases with increased hydrostatic head.

The above and other objects and advantages of the present invention will be more fully appreciated from the following description, claims and drawings in which:

FIG. 1 is a perspective view of the flexible tubing element which is located in the pumping section of the pump;

FIG. 2 is a perspective view of the peristaltic pump;

FIG. 3 is an enlarged detail view of a portion of the pumping tube as indicated in FIG. 1;

FIG. 4 is a longitudinal cross-sectional view of a section of the tubing element taken along lines 4—4 of FIG. 1;

FIG. 7 is an exploded view of an alternate embodiment in which the pump section is provided with an inlet occlusion valve;

FIG. 8 is a perspective view of the inlet occlusion valve in place;

FIG. 9 is a longitudinal cross-sectional view illustrating the pumping section tubing in cross-section in a closed position;

FIG. 10 illustrates in cross-section condition the inner tubing often assumes on full collapse; and FIG. 11 is a cross-sectional view of the inlet valve in the collapsed or closed position.

Figure 5:
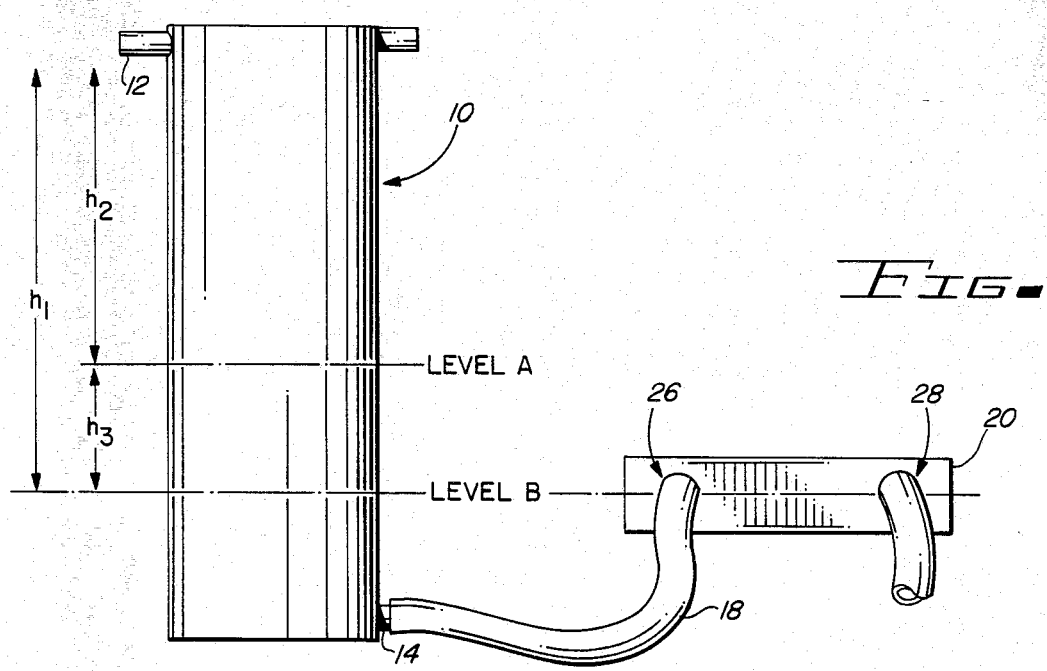
FIG. 5 shows the peristaltic pumping system of the present invention including a pump, connecting tubing and fluid reservoir.

Turning now to the drawings, FIGS. 1, 2 and 5 illustrate a peristaltic pumping system of the present invention. The system typically could be used to supply blood to a patient or a heart-lung machine, for renal dialysis or for supplying a suitable IV or other fluid to a patient of for therapeutic plasmapheresis. The same system may also be used for industrial pumping applications. The system includes a fluid reservoir generally designated by the numeral 10 which is shown as a generally cylindrical container having an inlet 12 to contain a suitable fluid such as blood from a filter. The inlet 12 is shown as being located near the upper end of the reservoir 10. An outlet 14 is provided near the bottom of the reservoir and is connected to inlet fitting 26 at pump 20 by upstream portion 18 of flexible tubing. Discharge tubing section 22 is provided for delivering fluid to the patient or to a subsequent component such as a dialyser and is connected to outlet fitting 28 at pump 20. The reservoir 10 and pump 20 are arranged so that outlet 14 of the reservoir is positioned at an elevation corresponding to or below the inlet fitting 26 of pump 20. The elevation of the pump inlet 26 is indicated by the horizontal line carrying the notation "Level B" in FIG. 5.

FIGS. 1 through 4 best illustrate the construction of the pump 20. Pump 20 includes a housing 30 shown as being generally rectangular having opposite side walls 32, 34, rear wall 36 and front wall 38. Housing 30 defines an interior chamber 40 having arcuate surface which forms a stator or raceway 42. Driveshaft 44 projects vertically into chamber 40 and carries rotor or head 46. Driveshaft 44 may be driven by a suitable motor, not shown, in conventional manner. Rotor 46 is provided with oppositely extending arms 48 which terminate at rollers 49.

Pumping element 50 extends in a general U-shape within the pump housing having a section engaging the stator or raceway. One end of pumping element 50 is secured to the pump housing 30 at inlet opening 45 in the front wall 38 by a suitable tube holder or clamp, as is well known. Similarly, the opposite end of pumping element 50 is secured by a tube holder or clamp to the housing at outlet opening 47. As driveshaft 44 rotates, rollers 49 are brought into contact with the pumping section and progressively compress the pumping element 50 against the raceway, forcing fluid through the pumping element to be discharged at the outlet. Pumps of the general type are typified by the Sarns Custom and Deluxe Roller Blood Pumps.

The construction of the novel pumping element forms an essential part of the present invention. As best seen in FIGS. 1, 3 and 4, pumping element 50 consists of an inner tube 56 and an outer tube 58. Inner tube 56 has a diameter less than the exterior diameter of outer tube 58, so an annular space 60 extends between the tubes. The tubes 56 and 58 may both be relatively thin-wall, made from a suitable elastic material such as rubber, elastomer, silicon rubber, silastic or similar material which is suitably flexible and chemically inert. The material further should have the capability of elastic memory and be adequately wear-resistant. The outer protective tube may, for example, be PVC for medical applications such as that sold under the trademark "Tygon" and designated S-50-HL having a $\frac{5}{8}$" I.D. × 13/16" O.D. Typical physical data from this tubing are:

| Test | Test Method | Result |
|---|---|---|
| 1. Durometer Harness, Shore A | ASTM D2240 | 63 ± 5 |
| 2. Tensile Strength, psi | ASTM D638 | 1850 ± 200 |
| 3. Tensile Stress a 100% Elongation, psi | ASTM D638 | 880 ± 40 |
| 4. Ultimate Elongation % | ASTM TMD 638 | 290 ± 50 |
| 5. Permanent Set, % | ASTM D412 | 76 ± 2 |
| 6. Tear Resistance lbs./in. | ASTM D1004 | 110 ± 15 |
| 7. Compression Set, Constant Deflection % | ASTM D395 | 53 ± 2 |
| 8. Compression Set, Constant Load % | ASTM D395 | 41 ± 2 |
| 9. Brittle Point, F | ASTM D746 | −55 ± 5 |
| 10. Specific Gravity | ASTM D792 | 1.20 ± .02 |
| 11. Abrasion Resistance, mg. loss/1,000 cycles | ASTM D1044 | 19 ± 10% |

The inner tubing may be, for example, polyurethane such as that sold under the trademark "TYGOTHANE" designated C-389-A with a $\frac{5}{8}$" O.D. and having a 0.015" wall. The inner tubing should have a low modulus of elasticity for example 100% modulus at 680 psi and ultimate 750% at 3800 psi. Other comparable materials may be used.

Fittings or connectors 26 and 28 are provided at the inlet and outlet, respectively, of the pump. The connectors are substantially identical so description of connector 26 is sufficient. Connector 26, as shown in FIGS. 3 and 4, consists of a body 72 having an intermediate rectangular portion 72 defined by spaced-apart flanges 74 and 76. The left end of connector 26 as viewed in FIG. 4, has an adaptor 78 provided with circumferential ribs 79 so that outer tubing 58 can be engaged thereabout in abutment with flange 74. Inner tube 56 extends through the cylindrical passage or lumen 85 of the connector and is reversely folded over the adaptor 80 at the exterior end of the connector at 81. The supply or suction tube 18 is engaged over the circumferential ribs 82 in abutment with flange 76 securing folded lip portion 81 in place. Apertures 83 in body 72 communicate the annular space 60 with atmosphere.

As mentioned above, connector 28 is similarly configured. Thus, flexible pumping section 50 extends within the raceway from the inlet to the outlet of the pump and is held in place by a conventional clamping mechanism, not shown, at the inlet and outlet. The annular airspace 60 extends from the inlet to the outlet being sealed at the reversely folded lip 81 at each of the connectors 26 and 28. Vent apertures 83 in body 72 communicate the annular airspace 60 between the tubes with atmosphere.

In operation, the pumping system of the present invention is connected as shown in FIG. 5. The pumping tubing section 50 is installed in the pump housing 30 and clamped in place with connectors 26 and 28 at the front wall of the pump. Suction tubing 18 is connected between the outlet 14 of the reservoir 10 and the pump inlet by engaging tubing over the ribs 82 of the connector and the folded lip 81 of the inner tube. Similarly, the outlet tubing section 22 is connected to the patient or to an appropriate component such as dialysis machine and to fitting or connector 28. Reservoir 10 is connected to a supply of fluid.

In the case of cardiopulmonary perfusion, reservoir 10 is connected to a supply of blood. As long as the blood level within the reservoir 10 remains above the level indicated by the horizontal line "Level A", a continuous supply of blood is discharged at the discharge 22 of the pump. The hydrostatic head in the region h2 within the reservoir maintains a sufficient pressure within the tube 56 to maintain the inner tube in a fully expanded position. However, as the hydrostatic head drops below the Level A and proceeds towards Level B, in the region h3, the pressure within the inner tubing portion 56 of the pumping section drops below the external pressure existing in the annular space 60. Under these conditions, the cross-sectional configuration of the interior tube tends to flatten until the passageway within the tube is entirely closed at a fluid level corresponding to the Level B. FIG. 5 illustrates the progressive collapse of the inner tube as the fluid head in the reservoir 10 reaches the upper limit of h3 and thereafter approaches Level B. As the inner tube flattens, the cross-sectional area decreases which restricts the available pumping volume. At Level B all flow through the tubing is terminated as the tube is fully collapsed. This prevents pumping of air into a patient's arterial circulation system as there is no volume to displace.

The new extracorporeal pumping device was evaluated in a laboratory test. The perfusion loop, with a double tube segment, was inserted into an extracorporeal circuit and threaded through a roller pump housing. The thin wall, collapsible, PVC inner tube was protected by a polyurethane outer tube as described above.

In vitro testing established the validity of this physical principle. An in vitro test circuit was constructed in order to compare the negative pressure that can be generated by both conventional arrangements and the perfusion loop of the invention. This simple test circuit consisted of a water filled reservoir 50 cm. above the pump inlet. Inflow occlusion was accomplished with a tubing clamp. With a conventional tubing, the roller pump, a Sarns custom roller pump, generated 680 mm. of mercury negative pressure with a conventional single tube. With the double tube perfusion loop of the invention as described, the inlet negative pressures was zero when occlusion occured.

Additional in vitro testing established the durability of the tubing arrangement of the invention as the test circuit was to run for five days without failure.

The perfusion loop was used in over twenty in vivo experiments for left heart bypass, cardiopulmonary bypass while using a bubble oxygenator, and cardiopulmonary bypass with direct venous cannulation and a membrane oxygenator. In two of these experiments direct venous cannulation was combined with the perfusion loop and membrane oxygenation. Canines were used in the in vivo testing procedures.

An extracorporeal blood flow probe was used to measure total blood flow through the apparatus. The circuit was primed with one liter of Lactated Ringers Solution with 50 mEq of sodium bicarbonate added to the prime. Both the 27 and 31 kilogram dogs were anesthetized with Surital and maintained on Fluothane anesthesia. A right thoracotomy was performed and a pursestring suture placed in the right atrial appendage. a #40 French venous cannula was then placed in the right atrium and advanced to a central position. Arterial cannulation was through both femoral arteries. Systemic arterial blood pressure was measured through the carotid artery using a blood pressure transducer. Central venous pressure was measured through a catheter advanced through a femoral vein into the inferior vena cava. The dogs were systemically heparinized with 10,000 units of sodium heparin. Perfusion was initiated after all clamps had been removed, setting the arterial pump speed at 50 revolutions per minute. This resulted in an output of the pum pf 3.3 liters per minute. Venous pressures were maintained at approxiamtely 5 cm. of water. Arterial blood pressure was maintained rrom 60 to 90 mm. of mercury. Extracorporeal circulation was continued for two and one-half hours at this blood flow rate. Arterial blood gasses were obtained. Ventilation through the membrane oxygenator was adjusted and sodium bicarbonate was administered as needed.

A hemodynamically stable perfusion could be maintained with the addition of fluids to the dog in order to sustain the central venous pressure at a level of 5 cc. of water. No additional adjustments were required in the arterial pump speed. Following a stable perfusion of two and one-half hours, some additional manipulations were carried out with one of these preparations. The output of the arterial pump was increased in ten revolutions per minute increments from 50 revolutions per minute to 100 revolutions per minute. Blood flow through the extracorporeal apparatus increased at this time from 3.3 liters per minute to 6.6 liters per minute. Incremental increases in blood flow rate were maintained for five minute intervals.

A stable and safe venous return could be maintained with blood flow rates as high as 6.6 liters per minute in a 27 kilogram dog. This flow rate of approximately 244 ml. per kilogram per minute far exceeds the basal blood flow requirements of this animal; however, it is interesting that such a high blood flow rate was possible with stable venous return and pressures in a normal range. From past canine experiments when using conventional bubble oxygenators with gravity venous return stable flow rates could not be maintained in this high range.

When using this extracorporeal apparatus, a servo mechanism is established. Increases in arterial blood flow also increased inflow to the pump just as the natural heart functions. The bypass system is closed, not containing air, thus reducing the possibility of an accidental infusion of air into the patient's arterial circulation. The perfusion apparatus requires a minimum of attention.

Durability tests thus far, although preliminary, have been conducted for a duration of five days of continuous operation. By combining the perfusion loop with direct venous cannulation and membrane oxygenation the perfusion loop eliminated the hazard of excessive inlet negative pressure and reduced the risk of air embolization. Secondarily, the perfusion loop established a physiologically stable venous return to the extracorporeal apparatus.

The construction of the pumping tube provides a number of substantial advantages. The outer tubing serves to protect the inner tubing from wear imposed by the rotating pump head. The outer tubing also prevents undue expansion of the inner tubing to prevent aneurysm and possible bursting of the interior section. Since the pumping section tubing is clamped in place and connected to the inlet and outlet lines by means of connectors, the pumping section can be easily removed and replaced after each procedure is completed.

Figure 6:
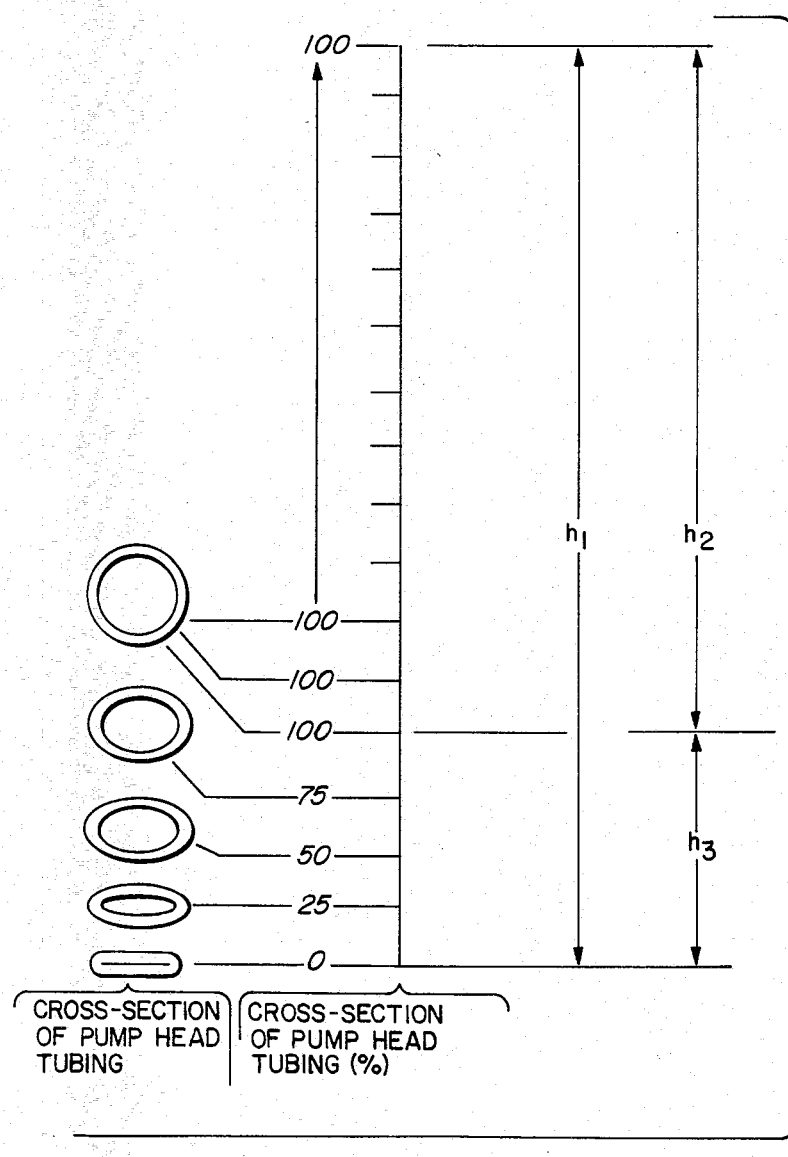
FIG. 6 is a graph schematically showing the relationship between the condition of the inner tube in the pumping section as compared with the hydrostatic head pressure existing in the fluid reservoir.

While the foregoing system works very well for many applications, further precaution to avoid entrainment of air may also be required in some applications. FIG. 6 illustrates the configuration of the collapsing cross-sectional tube area with decreased hydrostatic head. However, due to tube characteristics and system variables, many times the fully collapsed state of the tube actually will assume the shape shown in FIG. 10 in which the tube lumen has an exaggerated "FIG. 8" configuration. This configuration may allow some air to pass in the channels at either side of the collapsed tube even when full occlusion is achieved. Accordingly, the addition of an occluding inlet valve in some applications is highly desirable.

FIGS. 7 to 9 illustrate the addition of the inlet valve 100 to the pumping section of inner tube 58. A connector 102 is provided at the inlet end of the pumping section. The connector 102 has a projection 104 which is provided with annular serrations or projections 106 to tightly engage the interior diameter of inner tube 56. Outer tube 58 may be tightly engaged over the retaining projections and the inner tube as best seen in FIG. 9. Multiple fenestrations or openings 110 are provided in the outer tube to permit air to be admitted to the annulus between the inner and outer tubes.

Connector 102 is further provided with an oppositely extending cylindrical extension 112 which receives one end of the inlet valve body 101. The inlet valve body 101 is an elongated section of elastic material such as thin wall latex rubber or polyurethane which for perfusion applications would typically have a wall thickness of 0.015". As best seen in FIG. 7, the inlet valve is molded or constructed in such a fashion as cross-sectional is flat when no fluid pressure is applied to the lumen 116. The valve section has "memory" so that in the normal condition it assumes the flattened position as shown. The cross-section of the lumen increases with increased hydrostatic pressure head. The inlet valve, when in its flattened position, does not allow air to channel through the tubing gaps so that no subatmospheric pressure can be generated at the inlet of the perfusion loop. The opposite end of the inlet valve is provided with another fitting 120 and is provided with a projection 122 for receipt of connecting tubing. An annular retainer ring 128 may be provided over the cylindrical projection 112 and the outer diameter of the inlet valve body 102 which is stretched over projection 112. An outer casing 130 is provided with openings or fenestrations 132 which may extend between the oppositely disposed fittings 102 and 120. To retain the outer protective shielding or tubing in place, an appropriate flange 131 may be provided on each of the fittings 102 and 120.

Thus, in operation, the tubing from the fluid source such as the oxygenator is connected to projection 122 of fitting 120. The inlet valve 100 is positioned at the inlet to the tubing pumping section and is in the normally flattened closed position occluding all passage of air into the subsequent pumping section. As hydrostatic pressure increases, the area of the flattened tubing section will increase allowing fluid to pass into the subsequent pumping section. As hydrostatic pressure decreases, the tubing section and the inner tube of the pumping section will both tend to collapse. Upon the level of the fluid head reaching the level of the inlet to the tubing section, both the inner tube of the pumping section and the inlet valve will occlude. However, as pointed out above, the inner tube does not always fully collapse to a fully occluded position. However, since the valve body 101 has a normally fully flattened condition, full occlusion will be achieved at the inlet valve permitting any aspiration or perfusion of air into the pumping section and into the patient or other discharge location.

The peristaltic pump of the present invention provides a number of significant advantages in that damage or leakage to the system in the pumping section is minimized and the collapsibility of the inner tube serves to protect the system against accidental infusion of air. It will be obvious that the flexible tubing arrangement of the pumping section can be made of various materials and that different forms of connectors can be utilized. Also, it will be apparent that different styles and models of perfusion pumps can be used. Also, although the invention has been described with reference to medical applications the invention may be used with industrial applications such as handling and pumping corrosive or hazardous fluids. In such cases, the inner and outer tubes may be of different materials with the inner tube selected to have characteristics resistive to the transferred flud. The present invention would also have particular application in food and pharmaceutical handling processes where sterility is a requirement. The flexible tubing assembly can be sterilized and provided to the consumer in sterile packages.

It will be obvious to those skilled in the art to make various changes, alterations and modifications to the peristaltic pump of the present invention. To the extent that these changes, alterations and modifications do not depart from the spirit and scope of the appended claims, they are intended to be encompassed therein.

We claim:

1. A system for pumping liquid from a source, said system including a reservoir for fluid, a peristaltic pump in communication with said reservoir, said peristaltic pump having a raceway and a rotor rotatable along said raceway, said pump having an inlet and outlet and flexible pumping means connectable between said inlet and outlet and successively compressible by said rotor, said pumping means comprising:
    (a) an outer flexible tube defining an interior passageway extending between said inlet and outlet;
    (b) connectors at either end of said tube at said inlet and outlet;
    (c) an inner flexible tube having an inlet and outlet, said inner flexible tube having a lumen concentrically disposed within said outer tube, the exterior of said inner tube and the interior of said outer tube defining an annular space extending substantially from said inlet to said outlet, said inner tube being elastomeric and being selected to flatten in cross-section under decreasing hydrostatic pressure;
    (d) means for venting said annular space to atmosphere whereby said inner tube will begin to collapse when the fluid level in said reservoir approaches a first pre-determined level and whereby said inner tube collapses when the liquid level of said reservoir reaches approximately the elevation of the inlet of said pump whereby flow of liquid is halted and infusion of air is prevented; and (e) inlet occluding valve means at the inlet to said inner flexible tube having a normally closed position and openable in response to a positive pressure head.

2. A tubing section for peristaltic pumping system including a liquid reservoir, a peristaltic pump having a rotor and stator, said pump further having an inlet and outlet, said tubing section comprising:

(a) an outer flexible tube having an interior and exterior diameter, said tube adapted to extend between said pump inlet and outlet;

(b) a connector at each end of the tube at said pump inlet and outlet;

(c) an inner tube disposed within said outer tube having an interior and exterior diameter, said interior diameter defining a passageway for flow of liquid therethrough, the exterior of said inner tube and the interior of said outer tube defining an annular chamber;

(d) means for venting said annular chamber to atmosphere whereby when the liquid level in said reservoir drops below a pre-determined level, the inner tube will collapse terminating flow through said inner tube, thereby preventing infusion of air through said inner tube; and (e) inlet occluding means at the inlet to said tubing section wherein said occluding means comprises a normally closed and flattened elastic tube which will increase in cross-sectional area upon imposition of a hydrostatic head.

3. A method for the peristaltic pumping of a liquid from a source having a liquid level comprising:

(a) providing an outer elongated elastic tube having an interior and exterior diameter, said tube having an inlet and outlet;

(b) providing an inner compressible elastic tube disposed within said outer tube, said inner tube having an inlet and outlet and an interior and exterior diameter, said interior diameter defining a flow passageway for flow of a pumped liquid therethrough, the exterior of said inner tube and the interior of said outer tube defining an annulus extending substantially from the inlet to the outlet;

(c) providing a supply of liquid to said inner tube, said supply having a normal elevation above the inlet of the inner tube;

(d) providing occluding means at the inlet to said flow passageway, said occluding means being normally closed and openable in response to imposition of a positive hydrostatic head.

(e) venting said annulus to the atmosphere;

(f) applying compressive force to said outer tube to successively compress both said outer and inner tubes to move the liquid through said inner tube and collapsing said inner tube as the said liquid level drops below a pre-determined level and closing said inner tube to subtantially stop flow when the liquid level drops to a level approximately that of the said inlet to the inner tube.

* * * * *